(12) United States Patent
Faram

(10) Patent No.: US 9,566,397 B2
(45) Date of Patent: Feb. 14, 2017

(54) SMALL-VOLUME NEBULIZERS AND METHODS OF USE THEREOF

(71) Applicant: Joseph Dee Faram, Dallas, TX (US)

(72) Inventor: Joseph Dee Faram, Dallas, TX (US)

(*) Notice: Subject to any disclaimer, the term of this patent is extended or adjusted under 35 U.S.C. 154(b) by 338 days.

(21) Appl. No.: 14/067,045

(22) Filed: Oct. 30, 2013

(65) Prior Publication Data

US 2014/0048062 A1 Feb. 20, 2014

Related U.S. Application Data

(63) Continuation-in-part of application No. 11/748,907, filed on May 15, 2007.

(51) Int. Cl.
*A61M 11/00* (2006.01)
*A61M 15/00* (2006.01)
*A61M 16/20* (2006.01)
*A61M 11/02* (2006.01)
(Continued)

(52) U.S. Cl.
CPC .............. *A61M 11/00* (2013.01); *A61M 11/02* (2013.01); *A61M 15/0003* (2014.02); *A61M 15/004* (2014.02); *A61M 15/009* (2013.01); *A61M 15/0016* (2014.02); *A61M 15/0028* (2013.01); *A61M 15/0091* (2013.01); *A61M 16/0816* (2013.01); *A61M 16/20* (2013.01);
(Continued)

(58) Field of Classification Search
CPC ..... A61M 11/00; A61M 11/02; A61M 11/005; A61M 15/0028; A61M 15/0091; A61M 15/009; A61M 15/0018; A61M 15/002
See application file for complete search history.

(56) References Cited

U.S. PATENT DOCUMENTS 3,762,409 A 10/1973 Lester
3,774,602 A 11/1973 Edwards
3,945,378 A 3/1976 Paluch
(Continued)

FOREIGN PATENT DOCUMENTS

EP 1417982 A2 5/2004
GB 2055307 A 3/1981
(Continued)

OTHER PUBLICATIONS

Official Action issued in Japanese Patent Application No. 2010-508563, Mailing No. 80146, mailed on Feb. 20, 2015, and Translation of Official Action (6 pages).
(Continued)

*Primary Examiner* — Steven Douglas
*Assistant Examiner* — Kathrynn Lyddane
(74) *Attorney, Agent, or Firm* — Hitchcock Evert LLP

(57) ABSTRACT

The invention relates to a small-volume nebulizer with a valve system to provide lung physiotherapy during airway therapy with small-volume nebulizers. The valve system may be incorporated into a small-volume nebulizer. The small-volume nebulizer may be pre-filled with at least one unit-dose of medicine and hermetically sealed until use. The nebulizer may be sealed at the top with a removable cap that may be detached at the time of use and replaced with a patient connector. Likewise, the nebulizer may be sealed at the bottom with a bottom cap that is replaced with a gas source at the beginning of a therapeutic aerosol treatment.

**26

(51) Int. Cl.
*A61M 16/08* (2006.01)
*A61M 11/06* (2006.01)

(52) U.S. Cl.
CPC ............ *A61M 11/002* (2014.02); *A61M 11/06* (2013.01); *A61M 2205/123* (2013.01)

(56) References Cited

U.S. PATENT DOCUMENTS

| | | |
|---|---|---|
| 4,036,919 A | 7/1977 | Komendowski et al. |
| 4,150,071 A | 4/1979 | Pecina |
| 4,253,468 A | 3/1981 | Lehmbeck |
| 4,261,354 A * | 4/1981 | Nelson ................. A61M 15/06 128/203.23 |
| 4,534,343 A | 8/1985 | Nowacki et al. |
| 4,595,002 A | 6/1986 | Michaels et al. |
| 4,657,007 A | 4/1987 | Carlin et al. |
| 4,951,661 A | 8/1990 | Sladek |
| 5,429,122 A | 7/1995 | Zanen et al. |
| 5,490,630 A | 2/1996 | Hecker |
| 5,579,757 A | 12/1996 | McMahon et al. |
| 5,584,285 A | 12/1996 | Salter et al. |
| 5,813,401 A * | 9/1998 | Radcliff ............... A61M 16/208 128/200.14 |
| 5,823,179 A | 10/1998 | Grychowski et al. |
| 5,826,570 A | 10/1998 | Goodman et al. |
| 5,864,097 A | 1/1999 | Alvino |
| 6,044,841 A | 4/2000 | Verdun et al. |
| 6,257,231 B1 | 7/2001 | Shick et al. |
| 6,355,002 B1 | 3/2002 | Faram et al. |
| 6,363,932 B1 * | 4/2002 | Forchione ......... A61M 15/0086 128/200.14 |
| 6,390,090 B1 | 5/2002 | Piper |
| 6,412,481 B1 * | 7/2002 | Bienvenu .......... A61M 15/0086 128/200.21 |
| 6,510,846 B1 * | 1/2003 | O'Rourke ......... A61M 15/0086 128/200.21 |
| 6,632,842 B2 | 10/2003 | Chaundry et al. |
| 6,663,574 B2 | 12/2003 | Faram et al. |
| 6,679,250 B2 * | 1/2004 | Walker ................. A61B 5/0871 128/200.14 |
| 6,722,364 B2 | 4/2004 | Connelly et al. |
| 6,923,175 B2 | 8/2005 | Poole et al. |
| 6,994,083 B2 | 2/2006 | Foley et al. |
| 7,191,780 B2 | 3/2007 | Faram |
| 7,267,120 B2 | 9/2007 | Rustad et al. |
| 7,802,568 B2 | 9/2010 | Eicher et al. |
| 7,909,033 B2 | 3/2011 | Faram |
| 8,051,854 B2 | 11/2011 | Faram |
| 8,539,951 B1 * | 9/2013 | Meyer ................ A61M 16/0096 128/200.24 |
| 2001/0022279 A1 | 9/2001 | Denyer et al. |
| 2004/0031485 A1 | 2/2004 | Rustad et al. |
| 2005/0217666 A1* | 10/2005 | Fink .................... A61K 31/7036 128/200.14 |
| 2008/0078383 A1* | 4/2008 | Richards ............... A61M 16/08 128/203.12 |
| 2008/0283050 A1* | 11/2008 | Faram .................... A61M 11/02 128/200.21 |
| 2008/0283051 A1 | 11/2008 | Faram |
| 2009/0050141 A1 | 2/2009 | King et al. |
| 2009/0188500 A1 | 7/2009 | Faram |
| 2010/0095958 A1 | 4/2010 | King et al. |
| 2011/0100360 A1 | 5/2011 | Faram |
| 2011/0100364 A1 | 5/2011 | Faram |

FOREIGN PATENT DOCUMENTS

| | | |
|---|---|---|
| JP | 08-508671 | 9/1996 |
| JP | 2004-535845 A | 12/2004 |
| JP | 2005-520641 A | 7/2005 |
| JP | 56-66345 U | 2/2015 |
| WO | 95/20989 | 9/1996 |
| WO | 02/055142 A2 | 7/2002 |
| WO | 03/080149 A2 | 10/2003 |
| WO | 2006/006963 A2 | 1/2006 |
| WO | 2008/144358 A1 | 11/2008 |

OTHER PUBLICATIONS

Meyer, Harriett, "Antibacterial Agent in Some Asthma Medications Linked to Airway Constriction, UF Scientists Find." UF News, Jan. 11, 2001, 2 pages.

Grissinger, Matthew, RPh, FASCP, "Errors in the Making: Nearly Unreadable Labeling of Plastic Ampules for Nebulizing Agents", Medication Errors, P&T Journal, May 2005, vol. 30, No. 5, pp. 255-258.

O'Malley, Catherine A. et al., "A Day in the Life of Nebulizer: Surveillance for Bacterial Growth in Nebulizer Equipment of Children With Cystic Fibrosis in the Hospital Setting", Respiratory Care 2007, Mar. 2007, vol. 52, No. 3, pp. 258-262.

U.S. Department of Health and Human Services, Food and Drug Administration, Center for Drug Evaluation and Research (CDER), Center for Biologics Evaluation and Research (CBER) "Guidance for Industry, Container Closure Systems for Packaging Human Drugs and Biologics, Questions and Answers", May 2002, 6 pages.

Applyby, Julie, USA Today, DuoNeb®, "I Will Breathe Easier. Safety Concerns Grow Over Pharmacy-Mixed Drugs", 2005, 5 pages.

Hoisington ER, Chatburn RL, Stoller JK, Respiratory Institute, Cleveland Clinic Foundation, Cleveland, OH, A Comparison of Respiratory Care Workload With 2 Different Nebulizers., Abstract, PubMed, Respir Care, 2009, 1 page.

Chatburn RL, McPeck M., Section of Respiratory Care, Cleveland Clinic, Cleveland, OH, A New System for Understanding Nebulizer Performance., Abstract, PubMed, Respir Care, 2007, 1 page.

Jamalvi SW, Raza SJ, Naz F, Shamim S, Jamalvi SM., Department of Pediatrics, Jinnah Medical and Dental College, Karachi, Management of Acute Asthma in Children Using Metered Dose Inhaler and Small Volume Nebulizer., Abstract, PubMed, J Pak Med Assoc 2006, 1 page.

Colin Reisner, MD; Joseph Lee, RPh; Arthur Kotch, MD; and Gregory Dworkin, MD, Comparison of Volume Output from Two Different Continuous Nebulizer Systems, Annals of Allergy, Asthma & Immune, vol. 76, Feb. 1996, pp. 209-213.

Robert M. Kacmarek, Humidity and Aerosol Therapy, Chapter 71, Foundations of Respiratory Care, 1992, pp. 793-824, Churchill Livingstone Inc., New York, New York.

James B. Fink, MS, RRT, FAARC and Rajiv Dhand, MD, Respiratory Care Clinics of North America, Aerosol Therapy, Jun. 2001, pp. 131-340, vol. 7, No. 2, W.B. Saunders Company, A Harcourt Health Sciences Company, Philadelphia, Pennsylvania.

Bruce K. Rubin, MEng, MD, and James B. Fink MS, RRT, FAARC, Aerosol Therapy for Children, Respiratory Care Clinics of North America, Aerosol Therapy, Jun. 2001, pp. 175-213, vol. 7, No. 2, W.B. Saunders Company, A Harcourt Health Sciences Company, Philadelphia, Pennsylvania, (Article from the book cited in 11 above).

PCT International Search Report mailed on Sep. 29, 2008 for PCT/US08/63641.

* cited by examiner

SMALL-VOLUME NEBULIZERS AND METHODS OF USE THEREOF

CROSS-REFERENCE TO RELATED APPLICATION

This application claims the benefit of priority from U.S. patent application Ser. No. 11/748,907 filed on May 15, 2007, which is incorporated herein by reference.

FIELD OF THE INVENTION

The invention relates to small-volume nebulizers and components associated therewith.

BACKGROUND OF THE INVENTION

It is estimated that more than thirty million people each year are treated for respiratory diseases such as asthma and cystic fibrosis by aerosolizing medication in disposable, small-volume nebulizers, following which the medicine is then inhaled by a patient as a part of the patient's therapy. Bronchodilators, such as albuterol sulfate or ipratropium bromide, are typically used in order to improve airflow among patients with pulmonary maladies. Additional medicines, used in different forms of therapy or to treat different maladies, are also possible. As used herein, the terms "medicine" and "medication" shall refer to any one or a combination of substances used primarily in patient treatment and specifically excluding substances such as saline solution or water used primarily for the humidification of gases inhaled by a patient.

Pharmaceutical companies originally packaged these medicines in containers that held multiple doses. In order to initiate a patient treatment, the medicine needed to be transferred from the container to the treatment equipment such as a nebulizer. As the containers were repeatedly opened and closed, the medicine was exposed to bacterial contamination. In order to stem bacterial growth, chemicals such as benzalkonium chloride, or BAC, were added. However, it was eventually found that BAC itself may lead to airway constriction. See, Meyer, Harriet, "*Antibacterial Agent In Some Asthma Medications Linked To Airway Constriction, UF Scientists Find.*" UF News, Jan. 11, 2001. Thus, the use of BAC may have negated or at least reduced any positive effect the bronchodilators may have had.

In order to reduce bacterial contamination without adding potentially harmful antibacterial chemicals, pharmaceutical manufacturers began to package respiratory drugs in single-dose or "unit-dose" containers, thus removing the need to repeatedly open a container of medicine to dispense a dose. These unit-dose respiratory drugs are typically packaged in soft plastic containers often formed from low density polyethylene, or LDPE, in order to help control costs and to make the containers easy to open.

Typically, the medication is opened by twisting the top of the unit-dose container until the plastic gives way at a thin portion of plastic at the neck. The medication is then transferred into a disposable nebulizer by aiming the unit-dose container opening at the nebulizer housing opening, squeezing the soft plastic of the container until the contents have emptied, and then disposing of the empty unit-dose container.

However, unit-dose packaging was found to have inherent drawbacks. First, packaging costs increased over the previous bulk packaging due to the fact that each dose necessitated its own container. Second, the mere fact that the medicine must be transferred from a packaging container to a nebulizer or other treatment device is believed to carry an inherent risk of contamination. Further, it was found that LDPE is permeable to chemicals that have moderate to high vapor pressure, such as adhesives, varnishes, inks, and solvents, all of which are typically used in labeling and packaging materials. After it was determined that a number of different inhalation drugs packaged in LDPE unit-dose containers were contaminated with these chemicals, the industry moved away from printed paper-and-ink labels to embossed labeling with raised lettering. See, Grissinger, Matthew, "*Errors in the Making: Nearly Unreadable Labeling of Plastic Ampules for Nebulizing Agents.*" Medication Errors; P&T Journal May 2005; Vol. 30, No. 5, pp. 255-58.

Unfortunately, medication errors due to the poor legibility of embossed lettering on LDPE unit-dose containers have caused great concern in the medical community. See, Grissinger, Id. Drug names, concentrations, lot numbers, and expiration dates are embossed into the containers in the form of transparent, raised letters rendering them virtually impossible to read. This leads all too frequently to administering the wrong drug. Mistakes occur when unit-dose respiratory drugs are stored in refrigerated "respiratory bins" where a number of different drugs are typically placed. The risk of using the wrong medication is also increased when clinicians keep various unit-dose medications in their laboratory coat pockets, which is often the case.

The problem of potential medication errors associated with embossed labeling on unit-dose containers continues. Transferring medication from unit-dose containers takes time, adds to difficulty of use, introduces the potential for contamination during transfer, and runs the risk of under-dosing due to spillage. In addition, there still remains the added packaging cost associated with packaging each dose separately, not to mention environmental concerns associated with the disposal of millions of plastic unit-dose containers. Finally, even though LDPE plastic containers are more malleable than other plastics, these containers are still difficult to open, especially for elderly and arthritic patients.

Thus, there remains a need for packaging system for liquid medicines, which may be clearly labeled without risk of label-chemical contamination, which reduces the risk of contamination during transfer of medication from container to nebulizer, which reduces or eliminates the cost associated with each dose needing its own individual container, which saves the time associated with transferring medication from container to nebulizer, which reduces the need for disposal of millions of plastic unit-dose containers, which reduces the risk of under-dosing due to spillage, and which may still be more easily opened or used by elderly and arthritic patients.

Medical nebulizers are divided into two general categories: 1) large-volume, and 2) small-volume. Large-volume nebulizers are used, most often in hospital settings, to humidify gas, usually oxygen, to a patient. Large-volume nebulizers are utilized to add moisture to otherwise very dry gas by aerosolizing water, usually sterilized water with some mixture of saline in order to mimic the human body's salt content. Large-volume nebulizers often come pre-filled with various mixtures of sterile water and saline. Large-volume nebulizers have a reservoir volume greater than 100 mL. See Bruce K. Rubin & James B. Fink, Aerosol Therapy for Children, in 7 No. 2 RESPIRATORY CARE CLINICS OF NORTH AMERICA: AEROSOL THERAPY, 175, 187 (James B. Fink & Rajiv Dhand eds. 2001).

Small-volume nebulizers, also referred to as "hand-held nebulizers," are used for delivering medication to the lungs. Small-volume nebulizers are powered by high-pressure air or oxygen and are classified as pneumatic jet nebulizers. These devices are used for aerosolized medication therapy in both home and hospital settings. Although small-volume nebulizers are utilized in the delivery of a number of medications from analgesics to antibiotics, they are most often used to administer bronchodilators. Because they are for drug administration rather than humidification, small-volume nebulizers have medication reservoirs of 10 to 15 mL or less.

Small-volume nebulizers have come under scrutiny in recent years because of bacterial contamination. Traditionally, it has been common practice to clean and re-use disposable, single-patient-use, small-volume nebulizers. However, unless the nebulizer is completely sterilized it has been found that these "cleaned" nebulizers run the risk of growing such pathogens as *Pseudomonas aeruginosa*, *Staphylococcus aureus*, and *Haemophilus influenzae*, as well as other dangerous organisms. It is believed that contamination of the nebulizer occurs not only in spite of the cleaning, but may indeed be due to the cleaning itself. It is thought that poor cleaning techniques, inadequate drying, and the use of potable water sources may contribute to the contamination. Because of the risk of contamination and the fact that small-volume nebulizers are relatively inexpensive, especially when compared to the cost of nosocomial infections, many hospitals have come to the conclusion that it is safer and more prudent to dispose of the small-volume nebulizer soon after use. For example, it is currently a practice in many hospitals to utilize the same disposable nebulizer for twenty-four hours without cleaning, and then to dispose of it. See, O'Malley, Catherine A, et al. "*A Day in the Life of a Nebulizer: Surveillance for Bacterial Growth in Nebulizer Equipment of Children With Cystic Fibrosis in the Hospital Setting*." Respiratory Care 2007, Vol. 52, No. 3, pp. 258-62.

Respiratory patients are often treated with physiotherapies, physical therapies without medication, for the purposes of opening the airways, assisting in increased bi-level flow to enhance secretion movement, and to strengthen diaphragm muscles. These therapies generally fit into one of two categories depending upon the source of flows and pressures utilized in the therapy. One such category of devices utilizes flow and pressure generated by an external apparatus, such as intermittent positive pressure breathing devices (IPPB) such as the Mark 7®, MetaNeb®, or The Vest®. Each of these devices mechanically generates the flows and pressures necessary for the therapy. This category of device is more costly and intended for patients with a higher acuity level, many of whom do not have the ability to supply their own flows and pressures sufficiently to be effective.

The other category utilizes the flow and pressure generated by the patient. Examples of device in this category are positive expiratory pressure, Aerobika™, and Flutter®. Therapies that depend on flows and pressures created by the patient use either constant or intermittent resistance to the patient's flow. Positive expiratory pressure (PEP) is a constant resistance to patient exhalation, keeping backpressure on airways to keep them open. Some PEP devices also oscillate and are known as "oscillating positive expiratory pressure" (OPEP). Flutter® is another form of OPEP. The devices in this category are usually less costly and intended for those patients with less acuity and still strong enough to supply their own flow for the therapy.

The demands of the healthcare industry require devices and methods that deliver therapies appropriate to the patient's acuity, which cost less, require less time, and maximize efficacy. To this end, there are problems with the scarcity of choices among existing devices and methods for delivering these therapies.

Some small-volume nebulizers generate great variability in particle sizes, or heterodispersal, during the conversion of liquid medication into aerosol. Since various particle sizes tend to deposit in different locations within the lungs, it is desirable to reduce a wide variability of particle sizes to a tighter, more consistent size-range range, making the aerosol more monodispersed.

In addition, small-volume nebulizers waste medication during the exhalation phase of the breathing cycle. The medication is lost during a treatment in relation to the person's inspiratory to expiratory (I:E) ratio which typically ranges from 1:2 to 1:3. That is, if a patient has an I:E ratio of 1:2, for every 1 second the patient inhales 2 seconds are required to exhale. Accordingly, a small-volume nebulizer that creates continuous aerosol only delivers 1 second, or ⅓, of that aerosol to the patient and the remaining 2 seconds, or ⅔, is exhaled into the atmosphere. This waste of medication serves to further escalate the overall cost of healthcare to society.

Some research appears to indicate that healthcare workers, especially nurses and respiratory therapists, have a higher incidence of breathing maladies, such as asthma, than do other professionals. There is concern that these clinicians who work in environments where the delivery of aerosolized medications is commonplace may be put at risk by being forced to breathe the otherwise wasted medication mentioned above that remains suspended in ambient air.

Attempts have been made to create small-volume nebulizers that produce aerosol only during the inspiratory phase of the breath by utilizing complex valve systems that divert a high-pressure source gas away from the aerosolizing chamber. Other attempts to reduce the loss of medication include adding a series of one-way valves and additional reservoirs to retain the aerosol being produced during the patient's expiratory phase so that it can be delivered in a large bolus and the beginning of the next inspiratory phase of breath. Examples of these attempts are to be seen in a breathing circuit apparatus with a 50 cc reservoir (U.S. Pat. No. 5,584,285) and a reservoir bag apparatus (U.S. Pat. No. 6,390,090). However, the complexity of design increases the number parts to be manufactured as well as increasing the labor of assembly, thus increasing the cost of the device from existing small-volume nebulizers. In addition, the additional reservoirs and/or reservoir volume present the problem of additional surface area to which the aerosol can adhere, thus still wasting medication. In addition, the increased complexity and components may increase the likelihood of malfunctions in the operation of the device.

Another problem with delivering medication and non-medication therapies is the paucity of single devices that have the ability to deliver multiple therapies inexpensively. If a patient is deemed to require both medicated aerosol therapy and PEP physiotherapy typically two separate devices must be used. The need to use multiple devices to deliver the therapies results in added cost, added training time, added storage space, and may lead to an increased likelihood of contamination.

Attempts to combine physiotherapy devices and nebulizers, such as an oscillating PEP device (U.S. Pat. No. 8,539,951) and a small-volume nebulizer designed to manufacture aerosol only during inspiration (U.S. Pat. No. 6,044,841), require significant complexity and resulting high cost. In addition, the increased complexity may increase the likelihood of malfunctions in the operation of the device.

SUMMARY OF THE INVENTION

The present disclosure relates to small-volume nebulizers, components for use with small-volume nebulizers and methods of using the small-volume nebulizers and components therefore. In some embodiments, the present disclosure relates to a small-volume nebulizer pre-filled with medication so that the nebulizer may also serve as a medication container. It is comprised of a small-volume nebulizer containing medication, hermetically sealed, with removable caps at the top and bottom ports.

Some embodiments may include a valve system for a small-volume nebulizer comprised of at least one valve gate that opens and closes in response to a patient's breathing cycle. This valve system is placed at the top of the aerosolizing chamber at either the top or bottom of the chimney, between the patient opening and the aerosolizing chamber of the small-volume nebulizer.

In some embodiments, the present disclosure includes a means for choking the flow of the patient's inspiratory and expiratory effort. The means of choking patient flow also serves to deliver physiotherapy to the airways.

In some embodiments, the valve system and/or the means for choking the flow may be incorporated into the small-volume nebulizer. In some embodiments, the valve system and/or the means for choking the flow may be incorporated into a component that is attachable to the chimney of the small-volume nebulizer.

In some embodiments, the small-volume nebulizers include the nebulizer body or aerosolizing chamber, which includes a medication reservoir, a jet, a siphon and a baffle, a source of high-pressure gas, and an aerosol outlet port or chimney. High-pressure gas passes through the jet, which is a restricted orifice, and then flows through a siphon immersed in the medication, which is held in the medication reservoir. The siphoned medication is propelled at a high speed against a baffle, which is a surface that serves to break up the liquid medication into various sizes and cause larger aerosol particles to fall out of suspension.

In some embodiments, a "T" piece is attached to the aerosol outlet port or chimney. The "T" piece may include an airflow choking mechanism and a patient interface port or mouthpiece. In some embodiments, the aerosol output may include a valve system operational with a patient's breathing cycle.

In some embodiments, the improved small-volume nebulizer increases ease of use and time savings by eliminating a step in the procedure of administering aerosol medication.

In some embodiments, the improved small-volume nebulizer eliminates or reduces the costs associated with both disposable medicine containers and disposable nebulizers.

In some embodiments, the improved small-volume nebulizer eliminates or reduces the likelihood of contaminating medication during transfer of medication from a storage container to a treatment device such as a nebulizer.

In some embodiments, the improved small-volume nebulizer reduces the environmental burden associated with the disposal of unit-dose plastic containers and disposable nebulizers.

In some embodiments, the improved small-volume nebulizer reduces medication identity and volume dosing errors.

In some embodiments, the improved small-volume nebulizer reduces under-dosing due to spillage.

In some embodiments, the improved small-volume nebulizer increases the ease of opening medicine containers.

In some embodiments, the improved small-volume nebulizer reduces storage space required for both respiratory medications and small-volume nebulizers.

In some embodiments, the improved small-volume nebulizer minimizes egress of aerosolized medication from the aerosolizing chamber into the atmosphere during a patient's exhalation in order to reduce the waste of medication.

In some embodiments, the improved small-volume nebulizer reduces the flow of exhaled aerosolized medication into the atmosphere in order to further protect others from inhaling the medication for whom it is not intended.

In some embodiments, the improved small-volume nebulizer allows medication, which may escape during exhalation to be additionally filtered in order to further protect others from inhaling the medication for whom it is not intended.

In some embodiments, the improved small-volume nebulizer provides a non-drug, physiotherapy for the patient by creating inspiratory and expiratory flow resistance during a small-volume nebulizer treatment.

In some embodiments, the improved small-volume nebulizer targets the deposition of medication into particular regions of the lungs by reducing the heterodispersal of aerosol particle sizes.

In some embodiments, the improved small-volume nebulizer suppresses the aerosol being produced in the aerosol chamber from escaping that chamber during exhalation, making the medicated aerosol particles more monodispersed while adding the capability of simultaneous delivery of both physiotherapy and medicated aerosol therapy.

In some embodiments, the improved small-volume nebulizer reduces clinician-training time by reducing the number of devices needed to deliver multiple therapies.

In some embodiments, the improved small-volume nebulizer reduces respiratory storage space by reducing the number of devices needed to deliver multiple therapies.

In some embodiments, the improved small-volume nebulizer reduces costs by combining and simplifying said device, by reducing the number of parts needed to construct said device.

Additional aspects, advantages and features of the present invention are included in the following description of exemplary examples thereof, which description should be taken in conjunction with the accompanying figures, wherein like numerals are used to describe the same feature throughout the figures. All patents, patent applications, articles and other publications referenced herein are hereby incorporated herein by this reference in their entirety for all purposes.

A BRIEF DESCRIPTION OF THE DRAWINGS

FIG. 6A is a detailed side view of the valve system with the valve gate center pivot open.

FIG. 6B is a detailed frontal view of the valve system with the valve gate center pivot open.

DETAILED DESCRIPTION

FIG. 1 shows a side view of a preferred embodiment of the pre-filled, small-volume nebulizer of present invention. Each component depicted herein may be fabricated by means of injection molding of a plastic compound, of such material as polypropylene or other plastic compound with appropriate properties for housing medication and fabricating a nebulizer. The pre-filled, small-volume nebulizer may be comprised of a housing top 10, a housing bottom 12, a housing seal 14, pre-filled unit-dose of medication 16, a siphon 18, a jet 20, a baffle 22, an outlet port 24, an outlet port cap 26, an inlet port 28, an inlet port cap 30, an inlet one-way valve 32, an outlet port cap medication label 34.

The general structure and assembly of small volume nebulizers is known in the art. Housing top 10, housing bottom 12, siphon 18, jet 20, baffle 22, outlet port 24, and inlet port 28 are generally cylindrical or conical in shape and are generally co-axial with one another. Baffle 22 and outlet port 24 are typically formed as a part of housing top 10, while inlet port 28 is typically formed as a part of housing bottom 12. Typically, siphon 18 and jet 20 will be formed together in a single piece, with the resulting piece placed inside housing bottom 12. In typical prior art nebulizers, housing top 10 and housing bottom 12 are detachably joined by a threaded connection or by a press fit.

In the nebulizer of the present invention, prior to joining housing top 10 and housing bottom 12, all components of the nebulizer may be sterilized. Once the unit has been sterilized, medication 16 may be introduced into housing bottom 12. Finally, housing top 10 is connected to housing bottom 12 at housing seal 14, which is hermetically sealed by glue, sonic welding, or other known sealing techniques, to form nebulizer body 36.

To begin a medication therapy session with the pre-filled, small-volume nebulizer the patient or clinician may observe outlet port cap medication label 34 in order to verify the proper medicine is being used. Outlet port cap 26 may be removed, discarded, and replaced with either a mouthpiece attachment or some other type of patient interface common to the industry. To facilitate use of standard patient interface devices, outlet port 24 is of a shape, dimension and/or configuration commonly used in the industry. More specifically, outlet port 24 is preferably a generally cylindrical, tube having an outside diameter of between 15 and 30 millimeters, preferably between 20 and 25 millimeters, and most preferably of approximately 22 millimeters. Inlet port cap 30 may be removed and a source of gas under pressure such as an oxygen tube is connected to the inlet. During these maneuvers, pre-filled unit-dose of medication 16 within the nebulizer is prevented from exiting through inlet port 28 by one-way valve 32. As the therapy begins, gas under pressure enters inlet port 28 and travels through siphon 18 creating an area of relatively low pressure, which entrains at least a portion of pre-filled unit-dose of medication 16. The gas/medication mixture exits through jet 20, which directs the mixture such that it impinges against baffle 22 where the liquid medicine is broken up into small aerosol particles. The aerosol exits outlet port 24 and is delivered to the patient through a patient interface (not shown).

FIG. 2 depicts a side view of an alternate embodiment of the pre-filled, small-volume nebulizer of the present invention. In this embodiment outlet port 24 is sealed by piercable outlet port cap 38, which may either be removed or may be pierced at the time of use. In a preferred embodiment, the patient interface may be equipped with a mechanical appendage such as a spike which may be used to pierce outlet port cap 38 such that pre-filled unit-dose of medication 16 may be accessed without an operator or patient touching outlet port 24, thereby further reducing the likelihood of contamination. Furthermore, patient interface (not shown) may comprise a mouthpiece connected to a mouthpiece "T" which contains a spike for the purpose of saving time in the procedure of preparing for a therapy session. Outlet port 24 also contains an outlet port one-way valve 40, which allows aerosolized medication to flow out, but prevents retrograde flow in order to help defend against contamination.

The embodiment depicted in FIG. 2 further displays an alternate embodiment of the medication contained in the nebulizer. Specifically, in the embodiment depicted in FIG. 2, housing bottom 12 contains a plurality of pre-filled unit-doses of medication 16, and unit-dose completion demarcation marks 42. By providing a nebulizer body 36 pre-filled with multiple unit-doses of medicine, this embodiment of the present invention allows a patient or clinician to utilize the device for a predetermined period of time, twenty-four hours for example, without cleaning and reusing, and without disposing of the device earlier than is needed to prevent contamination. Unit-dose completion demarcation marks 42, allow a patient or clinician to determine when the delivery of a unit-dose of medication is complete and stop the therapy until it is time for the next.

FIG. 3 is a side view of a further alternate embodiment of the pre-filled, small-volume nebulizer of the present invention. In this embodiment, a compartment is provided within outlet port cap 26 for keeping a first component of a multi-component medication separate from a second component of a multi-component medication until use. This embodiment may find greatest application when the medicine to be administered is a mixture of one or more components, for example the mixture of Albuterol Sulfate and Ipratropium Bromide. However, mixing of medications can lead to additional problems associated with improper dosing and contamination. In some instances, it is believed that the useable life of these medicines once mixed is undesirably short. Therefore, in practice a patient or clinician generally mixes the medicines immediately prior to treatment. Of course, the increased handling of the medicine by a patient or clinician required during mixing may increase the likelihood of contamination and/or improper dosing. Therefore, by providing a pre-filled nebulizer which can separate multiple medication components until treatment, this embodiment of the present invention may greatly reduce these risks.

As shown in FIG. 3, outlet port cap 26 includes medication separation compartment 44, which may house a first component of a multi-component medication to be mixed with at least a second component of a multi-component medication at the time of use. Medication separation compartment 44 may be fabricated from a soft, malleable plastic composition such as a formulation of low density polyethylene. At the bottom of medication separation compartment 44 is a medication separation outlet gate 46 which is formed by fabricating a weak or thin portion of the plastic. As pressure is exerted at the top of medication separation compartment 44, medication separation outlet gate 46 breaks open and deposits its contents into housing bottom 12 where it mixes with pre-filled unit-dose of medication 16.

Figure 4:
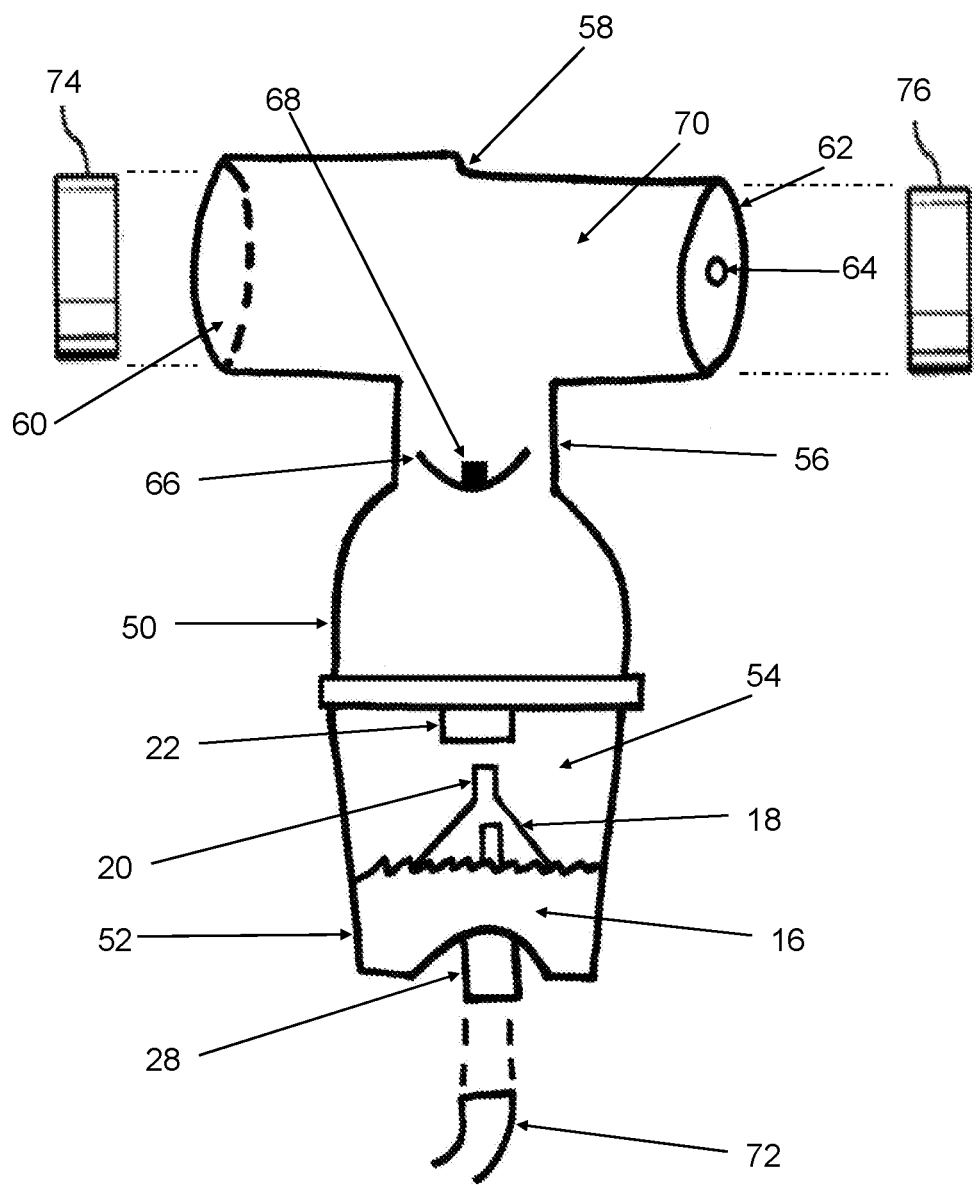
FIG. 4 is a side view of a preferred embodiment of the valve system incorporated integrally into a small-volume nebulizer.

FIG. 4 shows a side view of an embodiment of the valve system for small-volume nebulizers. Each component depicted herein may be fabricated with any variety of plastic compounds, such as polypropylene, or any compound with appropriate characteristics for housing and delivering aerosolized medication. The components may be manufactured by means of injection molding or any other means of manufacture.

Figure 1:
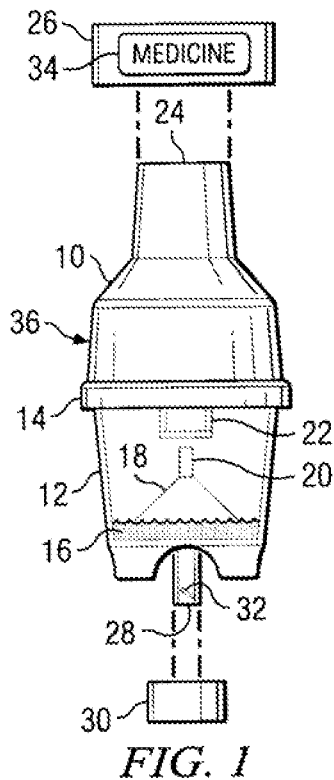
FIG. 1 is a side view of the pre-filled, small-volume nebulizer of present disclosure.
Figure 2:
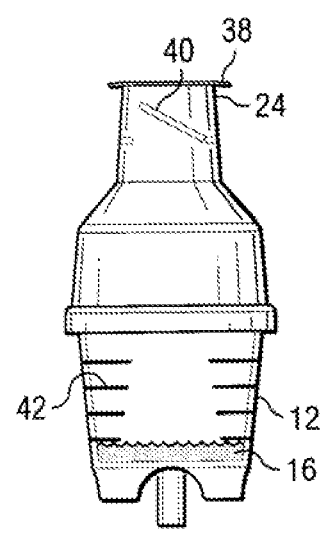
FIG. 2 is a side view of an alternate embodiment of the pre-filled, small-volume nebulizer of present disclosure with a piercable outlet port cap, a one-way valve at the outlet port, a plurality of pre-filled unit-doses of medication, and unit-dose completion demarcation marks.
Figure 3:
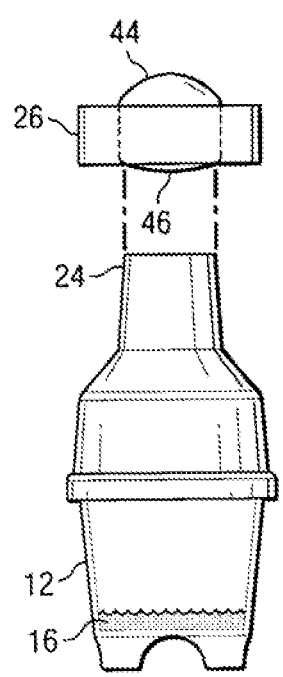
FIG. 3 is a side view of an alternate embodiment of the pre-filled, small-volume nebulizer of the present disclosure containing a separation compartment for a first component of a multi-component medication housed in the outlet port cap, and a second component of a multi-component medication housed in the nebulizer housing.

In this embodiment, the small-volume nebulizer 50 includes a medication reservoir 52 (sometimes referred to as a housing bottom), a aerosolizing chamber 54, a chimney 56 and a horizontal tube 58. Within the medication reservoir 52 and the aerosolizing chamber 54 of the small-volume nebulizer 50 are a baffle 22, a jet 20, and a siphon 18. The small-volume nebulizer 50 also includes a gas port 28. In the embodiment shown, medication 16 is also depicted in the medication reservoir 52. In some embodiments, the small-volume nebulizer 50 may be pre-filled with medication 16 as discussed further above. In such embodiments, the patient opening 60, the flow restrictor 64 and the gas port 28 may be hermetically sealed prior to use. For example, the small-volume nebulizer may include a first seal 74 removably engaged with the patient opening 60, a second seal (see cap 30 shown in FIG. 1) removably engaged with the inlet opening (gas port 28), and a third seal 76 removably engaged with ambient port 62 and covers the flow restrictor 64. First seal 74 and third seal 76 are shown as caps similar to cap 30 discussed further above.

The horizontal tube 58 includes a patient opening 60 at one end and an ambient port 62 at a second end. Within the ambient port 62 is a flow restrictor 64 to choke the ambient airflow during the patient's breathing cycle. The patient opening 60 may be a typical size, such as 22 mm, to allow it to connect directly to a patient mouthpiece or to be adaptable to other patient connections, such as tracheostomies and ventilator circuits. Ambient port 62 may also be a typical size to allow it to be connectable to a filter or ventilator circuit.

In this embodiment, within the chimney 56 is at least one valve gate 66 held in place by a valve gate center pivot 68. The valve gate 66 separates the aerosolizing chamber 54 of the small-volume nebulizer 50 from a proximal cavity 70 of the small-volume nebulizer 50. In this embodiment, the proximal cavity 70 is the open space within the horizontal tube 58 between the patient opening 60 and the ambient port 62 extending into the chimney 56 to the top of the valve gate 66. In the embodiment shown, the valve gate 66 is located near the bottom of chimney 56. In some embodiments, the valve gate may be located proximate to the top of the chimney 56. One skilled in the art will recognize that the placement of the valve gate 66 within the chimney 56 will vary and remain within the spirit and scope of the disclosure.

During operation, high-pressure gas is introduced into the gas port 28 from gas source tube 72 which is connected prior to use. Gas flows into the gas port 28 at an appropriate flow rate, typically ranging from 6 to 10 liters per minute, and is directed through jet 20, which has a narrowed orifice in order to accelerate the velocity of the gas. One skilled in the art will recognize that the gas will typically be oxygen, air and/or another gas and remain within the scope and spirit of the disclosure. In some embodiments, the gas will be provided by a compressed gas source. As the velocity increases, pressure within siphon 18 drops creating a suction, which serves to entrain medication 16. Medication 16 is hurled as spray against baffle 22. Baffle 22 is a surface that causes large particles to fall out of suspension, thus reducing the overall average particle size of the aerosol. After the sprayed medication encounters the baffle 22, the remaining particles are suspended within the body of the aerosolizing chamber 54 until at least one of the gates 66, located within chimney 56 and stabilized by valve gate center pivot 68, opens in order to allow egress of the aerosol particles from aerosolizing chamber 54 and into proximal cavity 70.

The valve gate 66 and the flow restrictor 64 in combination operate as a valve system for the small-volume nebulizer 50 providing physiotherapy and medicated therapy to a user with a single device. The valve system is in communication with the aerosolizing chamber 54 and includes the valve gate 66 positioned between the aerosolizing chamber 54 and the patient opening 60.

Valve gates 66 are made of an appropriate substance, such as neoprene, which has the qualities of being lightweight, flexible, and impervious to liquid. Valve gates 66 are in a normally closed position until forced open by a drop in pressure within proximal cavity 70. This drop in pressure is the result of a combination of events. First, as the patient inhales gas is drawn through the proximal cavity 70 from the atmosphere through flow restrictor 64. Based upon the restricted airflow, a vacuum or negative pressure effect is created within the proximal cavity 70. Flow restrictor 64 is an apparatus designed to choke or limit the airflow through the ambient port 62. In some embodiments, the flow restrictor 64 is an orifice within a circular plate fixed into ambient port 62, which may also be referred to as an orifice plate. To accomplish different flows and pressures various sizes of orifices may be used or a single orifice with an adjustable size may be used as well.

Orifice plates utilize Bernoulli's principal, which states that there is a relationship between the pressure and velocity of a gas or fluid. As velocity increases, pressure decreases and vice versa. As ambient gas is pulled through the orifice plate by the inhalation effort of the patient, the ambient gas converges in order to travel through the small orifice, and in turn increases in velocity. The increased velocity reduces the surrounding pressure, which assists in opening valve gates 66. Additional embodiments may utilize in the place of flow restrictor 64 a venturi and/or an adjustable spring restrictor (such as a Threshold™ PEP device). Additionally, an additional gas source may be introduced into proximal cavity 70 that utilizes a Coanda effect to assist in changing the pressures in response to the patient breathing effort.

The Coanda effect is the tendency of a fluid to be attracted to a nearby surface. Thus, flow from an additional gas source could increase or decrease pressure and flow as needed in response to a patient's inhalation or exhalation effort. With an additional gas delivery spout that presented dual curves, one toward patient opening 60 and one toward ambient port 62, the direction of this gas would be influenced by at least one of the inhalation going toward patient opening 60 and the exhalation going toward ambient port 62.

In some embodiments, ambient port 62 may be a suitable size within the industry, for example 22 mm OD (outside diameter) or 22 mm ID (inside diameter), to accommodate a respiratory filter such as those of common knowledge in the art. In some embodiments, such a respiratory filter may be used in conjunction with a flow restrictor 64 to filter the airflow into and/or out of the proximal cavity 70. In some embodiments, a respiratory filter may operate as a flow restrictor 64 due to airflow characteristics associated with the respiratory filter.

In addition, aerosol particle size is effected by at least one of the source gas flow rate, viscosity of the medication, size of the jet orifice, shape of the reservoir, number and characteristics the baffle(s), and subjecting the aerosol to a substantially tortuous pathway. The valve gate 66 in the open position during inhalation serves to create a tortuous pathway for the aerosol to travel as it exits from aerosolizing chamber 54. As the valve gate 66 is substantially closed during exhalation, it serves to substantially restrict egress of aerosol from aerosolizing chamber 54 and acts as an additional baffle. Accordingly, the valve gate 66 assists in making the medicated aerosol particles more monodispersed.

Figure 5:
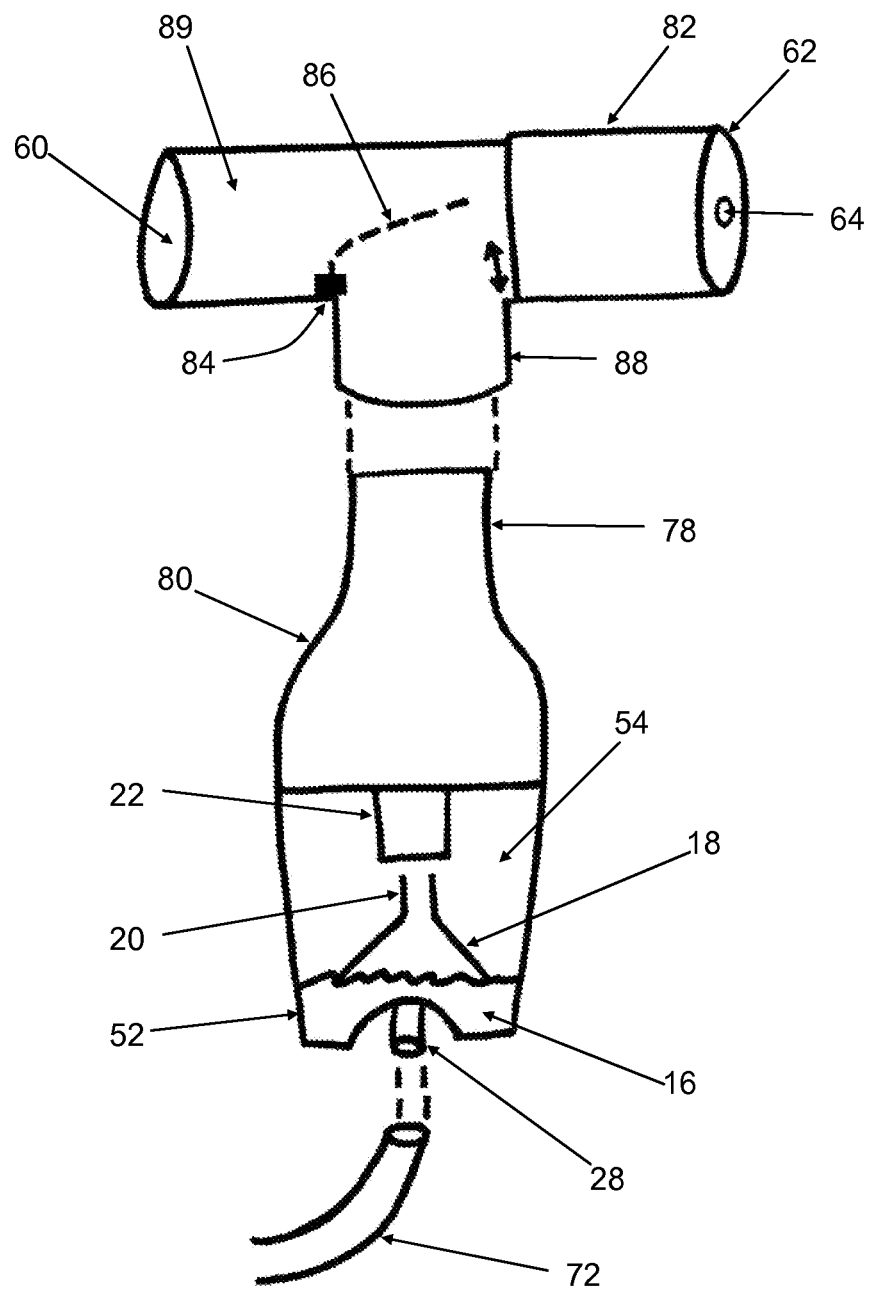
FIG. 5 is a side view of the valve system incorporated into a nebulizer "T" piece detachably connected to a small-volume nebulizer.

FIG. 5 is a side view of another embodiment of a small-volume nebulizer 80 and a "T" piece 82 that is connectable to the small-volume nebulizer 80. As discussed herein, each component depicted herein may be fabricated with any variety of plastic compounds, such as polypropylene, or any compound with appropriate characteristics for housing and delivering aerosolized medication. The components may be manufactured by means of injection molding or any other means of manufacture.

Similar to other embodiments described herein, the small-volume nebulizer 80 includes a medication reservoir 52, an aerosolizing chamber 54 and an aerosol output port 78 (also referred to as a chimney or outlet port). Within the medication reservoir 52 and the aerosolizing chamber 54 of the small-volume nebulizer 70 are a baffle 22, a jet 20, and a siphon 18. The small-volume nebulizer 80 also includes a gas port 28. In the embodiment shown, medication 16 is also depicted in the medication reservoir 52. In some embodiments, the small-volume nebulizer 80 may be pre-filled with medication 16 as discussed further above. In such embodiments, the aerosol output port 78 and the gas port 28 may be hermetically sealed prior to use.

In this embodiment, the "T" piece 82 includes a patient opening 60 at one end, an ambient port 62 at the end opposite from the patient opening 60 and a vertical "T" port 88 directed downward. Within the ambient port 62 is a flow restrictor 64 to choke the airflow during the patient's breathing cycle. In this embodiment, a valve gate 86 held in place by a valve gate side pivot 84 is located near the top of the vertical "T" port 88. In some embodiments, the valve gate 86 may be located proximate to the bottom of the vertical "T" port 88. One skilled in the art will recognize that the placement of the valve gate 86 within the vertical "T" port 88 will vary and remain within the spirit and scope of the disclosure.

The vertical "T" port 88 is designed to connect to the aerosol output port 78 of the small-volume nebulizer 80. In some embodiments, the vertical "T" port 88 is dimensioned to create a fitted connection with the top of aerosol output port 78. One skilled in the art will recognize that the vertical "T" port 88 may connect to the aerosol output port 78 in a variety of manners and remain within the spirit and scope of the disclosure. In some embodiments, the vertical "T" port 88 may include a spike or other mechanism to open a hermetic seal covering the top of the aerosol output port 78.

When the vertical "T" port 88 is connected to the aerosol output port 78, the valve gate 86 separates the aerosolizing chamber 54 of the small-volume nebulizer 80 from a proximal cavity 89 of the "T" piece 82. In this embodiment, the proximal cavity 89 is the area within the "T" piece 82 between the patient opening 60 and the ambient port 62 and above the top of the valve gate 86.

As discussed elsewhere herein, during operation, high-pressure gas is introduced into the gas port 28 from gas source tube 72 which is connected prior to use. Gas flows into the gas port 28 at an appropriate flow rate, typically ranging from 6 to 10 liters per minute, and is directed through jet 20, which has a narrowed orifice in order to accelerate the velocity of the gas. As the velocity increases, pressure within siphon 18 drops creating a suction, which serves to entrain medication 16. Medication 16 is hurled as spray against baffle 22. Baffle 22 is a surface that causes large particles to fall out of suspension, thus reducing the overall average particle size of the aerosol. After the sprayed medication encounters the baffle 22, the remaining particles are suspended within the body of the aerosolizing chamber 54 until the valve gate 86, located within vertical "T" port 88 and stabilized by valve gate side pivot 86, opens in order to allow egress of the aerosol particles from aerosolizing chamber 54 and into proximal cavity 89.

The valve gate 86 and the flow restrictor 64 in combination operate as a valve system for the small-volume nebulizer 80 providing physiotherapy and medicated therapy to a user with a single device. The valve system is in communication with the aerosolizing chamber 54 and includes the valve gate 86 positioned between the aerosolizing chamber 54 and the patient opening 60.

As discussed above, valve gate 86 is made of an appropriate substance, such as neoprene, which has the qualities of being lightweight, flexible, and impervious to liquid. The valve gate 86 is in a normally closed position until forced open by a drop in pressure within proximal cavity 89. This drop in pressure is the result of a combination of events. First, as the patient inhales gas is drawn through the proximal cavity 89 from the atmosphere through flow restrictor 64. Based upon the restricted airflow, a vacuum or negative pressure effect is created within the proximal cavity 89. Flow restrictor 64 is an apparatus designed to choke or limit the airflow through the ambient port 62. In some embodiments, the flow restrictor 64 is an orifice within a circular plate fixed into ambient port 62, which may also be referred to as an orifice plate. To accomplish different flows and pressures various sizes of orifices may be used or a single orifice with an adjustable size may be used as well.

As ambient gas is pulled through the orifice plate by the inhalation effort of the patient, the ambient gas converges in order to travel through the small orifice, and in turn increases in velocity. The increased velocity reduces the surrounding pressure, which assists in opening valve gate 86. In some embodiments, the flow restrictor 64 may be replaced by a venturi and/or an adjustable spring restrictor (such as a Threshold™ PEP or Threshold® IMT device) to regulate inspiratory and/or expiratory flow. Additionally, an additional gas source may be introduced into proximal cavity 89 that utilizes a Coanda effect to assist in changing the pressures in response to the patient breathing effort.

The flow from an additional gas source could increase or decrease pressure as needed in response to a patient's inhalation or exhalation effort. With an additional gas delivery spout that presented dual curves, one toward patient opening 60 and one toward ambient port 62, the direction of this gas would be influenced by at least one of the inhalation going toward patient opening 60 and the exhalation going toward ambient port 62.

In some embodiments, ambient port 62 may be a suitable size within the industry, for example 22 mm OD, to accommodate a respiratory filter such as those of common knowledge in the art. In some embodiments, such a respiratory filter may be used in conjunction with a flow restrictor 64 to filter the airflow into and/or out of the proximal cavity 89.

In some embodiments, a respiratory filter may operate as a flow restrictor 64 due to airflow characteristics associated with the respiratory filter.

In addition, aerosol particle size is effected by at least one of the source gas flow rate, viscosity of the medication, size of the jet orifice, shape of the reservoir, number and characteristics the baffle(s), and subjecting the aerosol to a substantially tortuous pathway. The valve gate 86 in the open position during inhalation serves to create a tortuous pathway for the aerosol to travel as it exits from aerosolizing chamber 54. As the valve gate 86 is substantially closed during exhalation, it serves to substantially restrict egress of aerosol from aerosolizing chamber 54 and acts as an additional baffle. Accordingly, the valve gate 86 assists in making the medicated aerosol particles more monodispersed.

Figure 6A:
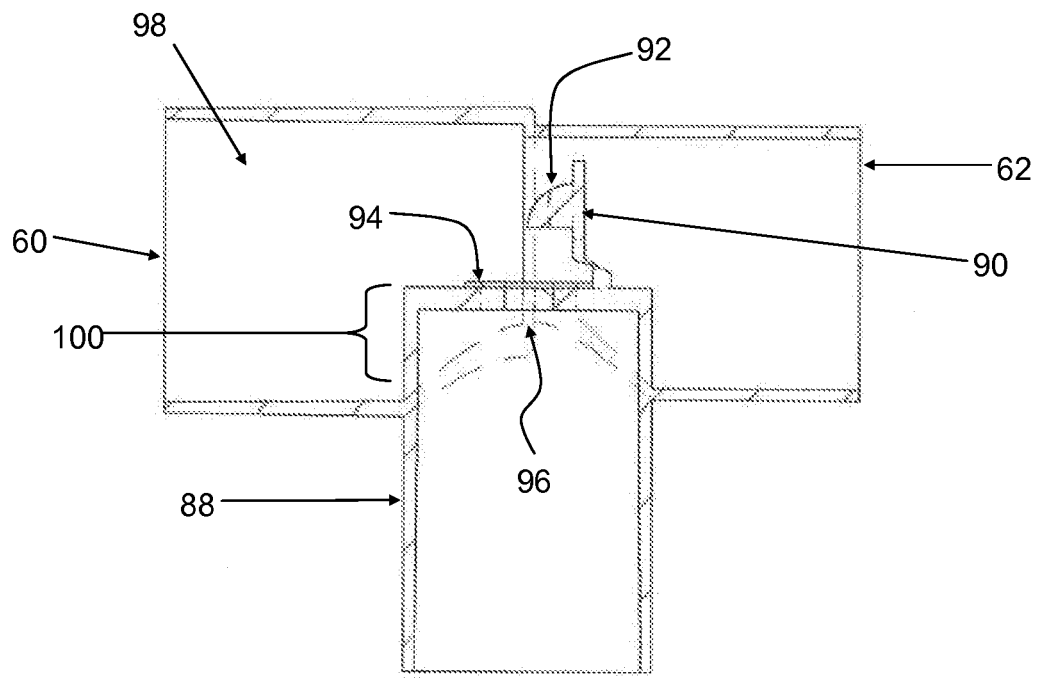
Figure 6B:
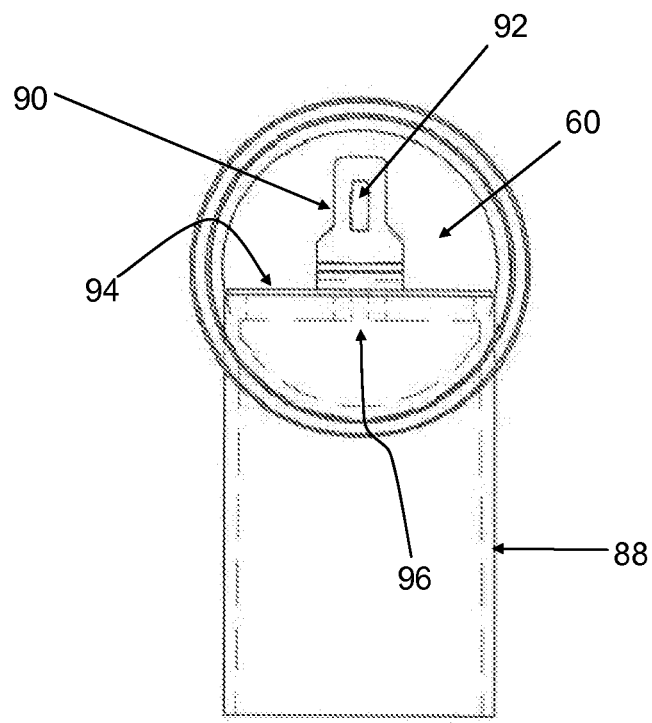

FIG. 6A and FIG. 6B different views of another embodiment of a "T" piece with the valve system with the valve gate center pivot 90 in an open position. FIG. 6A is a side view of the "T" piece and FIG. 6B is a frontal view of the "T" piece. In some embodiments, the design disclosed herein may be integrated into a small-volume nebulizer. For example, the vertical "T" port 88 may instead comprise the chimney of a small-volume nebulizer. As discussed herein, each component depicted herein may be fabricated with any variety of plastic compounds, such as polypropylene, or any compound with appropriate characteristics for housing and delivering aerosolized medication. The components may be manufactured by means of injection molding or any other means of manufacture.

In this embodiment, the "T" piece includes a patient opening 60 at one end, an ambient port 62 at the end opposite from the patient opening 60 and a vertical "T" port 88 directed downward. In some embodiments, a flow restrictor to choke the airflow during the patient's breathing cycle may be located within the ambient port 62. In this embodiment, a valve gate 94 may be held in place by a valve gate center pivot 90 which is shown in an open position. As discussed above, valve gate 94 is made of an appropriate substance, such as neoprene, which has the qualities of being lightweight, flexible, and impervious to liquid.

The valve gate 94 is located near the top of the vertical "T" port 88. In some embodiments, the valve gate 94 may be located proximate to the bottom of the vertical "T" port 88. One skilled in the art will recognize that the placement of the valve gate 94 within the vertical "T" port 88 will vary and remain within the spirit and scope of the disclosure.

The vertical "T" port 88 is designed to connect to an aerosol output port of a small-volume nebulizer. One skilled in the art will recognize that the vertical "T" port 88 may connect to the aerosol output port in a variety of manners and remain within the spirit and scope of the disclosure. As discussed elsewhere herein, the vertical "T" port 88 may include a spike or other mechanism to open a hermetic seal covering the top of an aerosol output port. When the vertical "T" port 88 is connected to an aerosol output port, the valve gate 94 separates the aerosolizing chamber of a small-volume nebulizer from a proximal cavity 98 of the "T" piece. In this embodiment, the proximal cavity 98 is the area within the "T" piece between the patient opening 60 and the ambient port 62 and above the top of the valve gate 94.

In the embodiment shown, the valve gate center pivot 90 is shown in the open position. Prior to administering a therapy using the "T" piece, the valve gate center pivot 90 will be latched into a closed position. In some embodiments, the valve gate center pivot 90 will be latched during manufacture of the "T" piece. In this embodiment, the valve gate center pivot 90 includes a tab 92. When closed, the tab 92 passes through the valve gate 94 and engages with a slot 96 built in to a mount located in this embodiment at the top of the vertical "T" port 88. The structure for the mount design includes the slot 96 for engagement with the tab 92 of the valve gate center pivot 90 and one or more openings under the valve gate 94. As discussed further herein, medicated aerosol from an attached small-volume nebulizer passes through the openings when the valve gate 94 opens in conjunction with a patient's inhalation. When the valve gate 94 closes in conjunction with a patient's exhalation, the valve gate 94 creates a seal with the mount. In some embodiments, the mount and valve gate 94 may be located at other locations within the vertical "T" port 88.

The connection created through engagement of the tab 92 with the slot 96 is designed to hold the valve gate 94 in place during operation of the "T" piece. Accordingly, the connection must be sufficient to withstand the various effects of the patient's breathing cycle, the pressures created within the attached small-volume nebulizer and any other effects created during the set-up and operation of the device. One skilled in the art will recognize that various connections may be employed which meet the operational necessities of the connection, such as a friction connection, a snap-connection, a locking connection, adhesives, fitted connections, pin connections, and other connections.

In this embodiment, the "T" piece is depicted as a "drool T" and is designed with a raised section 100 which limits the ability of a patient's drool to feed back into the small-volume nebulizer through the valve gate 94 and the vertical "T" port 88. One skilled in the art will recognize that other designs may be operable to provide anti-drool or drool catching characteristics and remain within the scope and spirit of the disclosure.

As discussed elsewhere herein, during operation, medication is aerosolized within a small-volume nebulizer and the particles remain suspended within the body of the small-volume nebulizer until the valve gate 94 opens in order to allow egress of the aerosol particles from the small-volume nebulizer and into proximal cavity 98. The valve gate 94 limits the escape of medication during exhalation conserving medicine. The valve gate 94 is in a normally closed position until forced open by a drop in pressure within proximal cavity 98. In some embodiments, this drop in pressure is the result of a combination of events. First, as the patient inhales gas is drawn through the proximal cavity 98 from the atmosphere through a flow restrictor. Based upon the restricted airflow, a vacuum or negative pressure effect is created within the proximal cavity 98. A flow restrictor is an apparatus designed to choke or limit the airflow through the ambient port 62. To accomplish different flows and pressures various designs of flow restrictors may be utilized. In some embodiments, a series of interchangeable flow restrictors which are compatible with the ambient port 62 may be available to customize the flow and pressure characteristics.

As ambient gas is pulled through the flow restrictor by the inhalation effort of the patient, the ambient gas converges in order to travel through the flow restrictor, and in turn increases in velocity. The increased velocity reduces the surrounding pressure, which assists in opening valve gate 94. In some embodiments, the flow restrictor may be replaced by a venturi and/or an adjustable spring restrictor (such as a Threshold™ PEP or Threshold® IMT device) regulate inspiratory and/or expiratory flow.

In some embodiments, an additional gas source may be introduced into proximal cavity 98 that utilizes a Coanda effect to assist in changing the pressures in response to the patient breathing effort. The flow from an additional gas source could increase or decrease pressure as needed in response to a patient's inhalation or exhalation effort. With an additional gas delivery spout that presented dual curves, one toward patient opening 60 and one toward ambient port 62, the direction of this gas would be influenced by at least one of the inhalation going toward patient opening 60 and the exhalation going toward ambient port 62.

In some embodiments, ambient port 62 may accommodate a respiratory filter such as those of common knowledge in the art. Such a respiratory filter may be used in conjunction with a flow restrictor to filter the airflow into and/or out of the proximal cavity 98. In some embodiments, a respiratory filter may operate as a flow restrictor due to airflow characteristics associated with the respiratory filter.

In addition, aerosol particle size is effected by at least one of the source gas flow rate, viscosity of the medication, size of the jet orifice, shape of the reservoir, number and characteristics the baffle(s), and subjecting the aerosol to a substantially tortuous pathway. The valve gate 98 in the open position during inhalation serves to create a tortuous pathway for the aerosol to travel as it exits from a connected small-volume nebulizer. As the valve gate 94 is substantially closed during exhalation, it serves to substantially restrict egress of aerosol from a connected small-volume nebulizer and acts as an additional baffle. Accordingly, the valve gate 94 assists in making the medicated aerosol particles more monodispersed.

The invention being thus described and further described in the claims, it will be obvious that the same may be varied in many ways. Such variations are not to be regarded as a departure from the spirit and scope of the invention and all such modifications as would be obvious to one skilled in the art are intended to be included within the scope of the apparatus, system, process and computer program product described.

What is claimed:

1. A pre-filled, small-volume nebulizer comprising:
   a small-volume nebulizer body comprising:
      an aerosolizing chamber, wherein contained within said aerosolizing chamber is at least one of a siphon, a jet, and a baffle,
      a chimney at the top of said aerosolizing chamber, wherein contained within said chimney is a valve gate which, during operation of the small-volume nebulizer by a user, opens with an inhalation by the user and closes with an exhalation by the user;
      a patient interface tube at the top of said chimney, wherein the patient interface tube includes a patient opening operable to connect with a patient interface component and an ambient port having a flow restrictor, wherein, during said operation of the small-volume nebulizer by said user, said flow restrictor is configured to restrict inhalation airflow during said inhalation by the user causing a drop in pressure within said patient interface tube and said flow restrictor restricts exhalation airflow during said exhalation by the user, wherein said inhalation airflow and said exhalation airflow passes through said flow restrictor, and
      an inlet opening operable to connect with a gas input;
   a first seal removably engaged with said patient opening;
   a second seal removably engaged with said inlet opening;
   a third seal removably engaged with said ambient port and covers the flow restrictor, wherein said first seal, said second seal and said third seal are configured to be unsealed during said operation of the small-volume nebulizer by said user; and
   a unit-dose of medication contained within said small-volume nebulizer body.

2. The pre-filled, small-volume nebulizer according to claim 1, wherein said patient interface component comprises a mouthpiece.

3. The pre-filled, small-volume nebulizer according to claim 1, wherein said medication is a first component of a multi-component medication, further including a first compartment containing a second component of said multi-component medication.

4. The pre-filled, small-volume nebulizer according to claim 1, further comprising a plurality of said unit-doses of medication.

5. The pre-filled, small-volume nebulizer according to claim 4, further comprising unit-dose completion demarcation marks.

6. The pre-filled, small-volume nebulizer according to claim 1, wherein at least one of said first seal, said second seal and said third seal is comprised of a piercable seal.

7. The pre-filled, small-volume nebulizer according to claim 1, wherein said flow restrictor is fixed within said ambient port.

8. A small-volume nebulizer comprising:
   a small-volume nebulizer body comprising:
      an aerosolizing chamber, wherein contained within said aerosolizing chamber is at least one of a siphon, a jet, and a baffle,
      a chimney at the top of said aerosolizing chamber, wherein contained within said chimney is a valve gate;
      a patient interface tube at the top of said chimney, wherein the patient interface tube includes a patient opening operable to connect with a patient interface component and an ambient port having a flow restrictor comprising an orifice plate, and wherein said patient opening is located at a first end of said patient interface tube, said ambient opening is located at a second end of said patient interface tube and said chimney is located between said first end and said second end of said patient interface tube, and
      an inlet opening operable to connect with a gas input;
   wherein, during operation of the small-volume nebulizer by a user, medication is aerosolized within said aerosolizing chamber and remains within said aerosolizing chamber until said valve gate opens based upon an inhalation by the user, and said valve gate closes with an exhalation by the user suppressing the egress of aerosolized medication from said aerosolizing chamber, and wherein said flow restrictor restricts inhalation airflow during said inhalation by the user and said flow restrictor restricts exhalation airflow during said exhalation by the user, wherein said orifice plate comprises a plate with an orifice passing through the plate, and wherein during operation, said inhalation airflow and said exhalation airflow passes through said orifice.

9. The small-volume nebulizer according to claim 8, wherein said patient interface component comprises a mouthpiece.

10. The small-volume nebulizer according to claim 8, wherein said orifice plate is in a removable connection with said ambient port.

11. The small-volume nebulizer according to claim 8, further comprising at least one dose of a medication and at least one hermetic seal associated with said patient interface opening, said inlet opening and said ambient port.

12. The small-volume nebulizer according to claim 8, wherein said flow restrictor comprises a respiratory filter.

13. The small-volume nebulizer according to claim 8, further comprising a respiratory filter in a removable connection with at least one of said flow restrictor and said ambient port.

14. The small-volume nebulizer according to claim 8, wherein said valve gate comprises a flexible material attached to a mount located within said chimney by a valve gate center pivot which is engaged with said mount.

15. The small-volume nebulizer according to claim 8, wherein said orifice is configured to cause said inhalation airflow passing through said orifice to increase velocity and reduce pressure within said patient interface tube.

16. A valve system apparatus for attachment to a small-volume nebulizer comprising:
a valve system body comprising:
a vertical port operable to connect with an aerosol output port of said small-volume nebulizer that is operable to produce aerosol, wherein contained within said vertical port is a valve gate which is operable to open based upon an inhalation by a user and operable to close based upon an exhalation by the user during operation of said valve system apparatus with said small-volume nebulizer; and
a patient interface tube at the top of said vertical port, wherein the patient interface tube includes a flow restrictor at a first end and a patient opening at a second end that is operable to connect with a patient interface component, wherein said vertical port is between said first end and said second end of said patient interface tube, and wherein said flow restrictor is configured to restrict inhalation airflow during said inhalation by the user causing a drop in pressure within said patient interface tube and said flow restrictor restricts exhalation airflow during said exhalation by the user, wherein said inhalation airflow and said exhalation airflow passes through said flow restrictor.

17. The valve system apparatus according to claim 16, wherein said patient interface component comprises a mouthpiece.

18. The valve system apparatus according to claim 16, wherein said flow restrictor comprises an orifice plate, wherein said orifice plate comprises a plate with an orifice passing through the plate, and wherein during operation, said inhalation airflow and said exhalation airflow passes through said orifice.

19. The valve system apparatus according to claim 18, wherein said orifice plate is in a removable connection with an ambient port.

20. The valve system apparatus according to claim 18, wherein said orifice is configured to cause said inhalation airflow passing through said orifice to increase velocity and reduce pressure within said patient interface tube.

21. The valve system apparatus according to claim 16, further comprising a seal opening apparatus, wherein said seal opening apparatus operates to open a seal associated with the aerosol output port of the small-volume nebulizer when said valve system apparatus is attached to said small-volume nebulizer.

22. The valve system apparatus according to claim 16, wherein said flow restrictor comprises a respiratory filter.

23. The valve system apparatus according to claim 16 further comprising a respiratory filter in a removable connection with at least one of said flow restrictor and said ambient port.

24. The valve system apparatus according to claim 16, wherein said valve gate comprises a flexible material attached to a mount located within said vertical port by a valve gate center pivot which is engaged with said mount.

25. A method of administering aerosolized medicine and a lung physiotherapy utilizing a small-volume nebulizer comprising the steps of:
providing said small-volume nebulizer containing at least one unit-dose of medicine with a valve system apparatus, wherein said small-volume nebulizer comprises an aerosolizing chamber containing at least one of a siphon, a jet, and a baffle, and said valve system apparatus comprises a patient interface opening, a flow restrictor and a valve gate located between said aerosolizing chamber and a patient interface component, and wherein said patient interface opening is located at a first end of a patient interface tube and said flow restrictor is located at a second end of said patient interface tube;
engaging said patient interface component with said patient interface opening;
connecting a source of gas under pressure to said nebulizer; and
delivering aerosolized medicine and lung physiotherapy to a patient, wherein said valve gate opens based upon an inhalation by said patient to deliver said aerosolized medicine and closes based upon an exhalation by said patient to suppress the egress of aerosolized medicine, wherein during said inhalation by said patient said flow restrictor restricts inhalation airflow causing a drop in pressure within said patient interface tube, and wherein said flow restrictor facilitates a non-medicated lung physiotherapy by restricting exhalation airflow during said exhalation by the patient, wherein said inhalation airflow and said exhalation airflow passes through said flow restrictor.

26. The method of claim 25 wherein the medicine to be administered has been prescribed, further comprising the steps of:
observing a medication label affixed to said small-volume nebulizer which identifies a medicine contained within said nebulizer;
verifying that the medicine identified in the medication label agrees with said prescribed medicine.

* * * * *